United States Patent [19]

Ikenaga et al.

[11] Patent Number: 6,139,882
[45] Date of Patent: Oct. 31, 2000

[54] METHOD OF PRODUCING IRON-WHEY-PROTEOLYSATE COMPLEX

[75] Inventors: Akihito Ikenaga, Oomiya; Kaoru Sato, Kamifukuoka; Toshio Sakurai, Tokyo; Toshiaki Uchida, Kawagoe, all of Japan

[73] Assignee: Snow Brand Milk Products Co., Ltd., Hokkai-do, Japan

[21] Appl. No.: 09/371,417

[22] Filed: Aug. 10, 1999

[30] Foreign Application Priority Data

Aug. 11, 1998 [JP] Japan .................................. 10-226453

[51] Int. Cl.⁷ .......................... A23K 1/175; A23L 1/304
[52] U.S. Cl. ............................ 426/74; 426/42; 426/805; 530/395; 530/400; 424/535; 556/138; 514/6
[58] Field of Search ................................ 426/74, 42, 805; 530/395, 400; 424/535; 556/138; 514/6

[56] References Cited

U.S. PATENT DOCUMENTS

| 5,098,722 | 3/1992 | Tanaka et al. ............................. 426/74 |
| 5,116,953 | 5/1992 | Dosako et al. ........................... 530/400 |
| 5,606,086 | 2/1997 | Dosako et al. ........................... 556/138 |

FOREIGN PATENT DOCUMENTS

| 0 409 252 A2 | 1/1991 | European Pat. Off. . |
| 0 409 252 A3 | 1/1991 | European Pat. Off. . |
| 58-020159 | 2/1983 | Japan . |
| 4-365444 | 12/1992 | Japan . |
| 07017875 | 1/1995 | Japan . |
| 07304798 | 11/1995 | Japan . |
| 7-304798 | 11/1995 | Japan . |
| 09084522 | 3/1997 | Japan . |
| 09111140 | 4/1997 | Japan . |

*Primary Examiner*—Chhaya D. Sayala
*Attorney, Agent, or Firm*—Knobbe, Martens Olson & Bear, LLP

[57] ABSTRACT

A carbonate- and/or bicarbonate-iron-whey-proteolysate complex includes 1 to 1,000 atoms of iron and one or more molecules of carbonate and/or bicarbonate per one molecule of whey-protein as measured before whey proteolysis, and exhibits no specific iron taste. The carbonate- and/or bicarbonate-iron-whey proteolysate complex is used in drugs, foods, drinks, and animal feed for the purposes of an iron supplement for treatment and prevention of anemia.

10 Claims, 2 Drawing Sheets

METHOD OF PRODUCING IRON-WHEY-PROTEOLYSATE COMPLEX

BACKGROUND OF THE INVENTION

1. Field of the Invention

The invention relates to a complex including iron and whey protein derivative, and particularly to an iron-whey-proteolysate complex using a carbonate and/or bicarbonate. The complex is characterized by no particular iron taste and used in drugs, foods, drinks, and animal feed for the purpose of an iron supplement. The present invention also relates to a method of producing the above complex.

2. Description of the Related Art

Whey is a by-product being formed from the production process of cheese and casein, and a desirable food material rich in protein, mineral, lactose, and other trace constituents. Compared with casein, whey protein is superior in amino acid composition, and therefore, it can be used as a source of protein constituting a highly nutritious food. Due to the increase in consumption of cheese in recent years, the output of whey has increased as well. Developing further usage of whey is now called for from the point of protecting the environment and using a natural resource.

The amount of iron intake from the Japanese diet has almost leveled off since 1975, with a fluctuations in the sufficiency of the daily-recommended amount at around 100 percent. Iron may be one of the nutrients in our diet which we should pay attention to. In addition, worldwide, iron is the nutrient that tends to be lacking in the regular diet. In particular, it is necessary to supply iron supplements in drink, food and tablets for iron deficient people or pregnant women. Adding an iron salt, such as iron sulfate and iron citric acid, to foods and drinks, however, causes a specific unpleasant iron taste, and may irritate or damage the stomach lining. Therefore, the quantity of iron added has been limited. As hemoferrum of organoferrum also has problems of flavor, such as metal flavor or bloody taste, the addition of those ingredients to foods and drinks has been limited. To promote iron absorption, adding milk casein, amino acids, and caseinophophopeptide has been tested according to Japanese Patent Application Laid-open No. 59-162843. These products, however, have problems such as not eliminating specific iron flavors, and if the products are used simply in a limited quantity that does not give the specific iron flavors, the products are not effective.

SUMMARY OF THE INVENTION

The present inventors developed a carbon and/or bicarbonate-iron-lactoferrin substance complex having no specific iron taste when binding iron to a lactoferrin substance via a carbonate or bicarbonate (Japanese Patent Application Laid-open No. 7-304788). In addition, they invented a carbonate- and/or bicarbonate-iron-casein substance complex by binding iron to a casein substance in a manner similar to the above (Japanese Patent Application Laid-open No. 9-77793).

The present invention has exploited an iron-whey-proteolysate complex. As the present inventors searched for new technologies for using whey protein, it was found that whey protein hydrolysate, whey protein hydrolyzed by proteolytic enzyme, also has similar characteristics to lactoferrin substances and casein substances which can bind iron by using a carbonate or bicarbonate as a medium. In addition, the present inventors found that these carbonate- and/or bicarbonate-iron-whey proteolysate complexes contain iron in high ratios, yet do not have a specific iron taste, leading to completion of the present invention. Therefore, in an embodiment, the present invention is to provide a carbonate- and/or bicarbonate-iron-whey proteolysate complex having no specific iron taste. Whey proteolysate complex can bind iron by using a carbonate or bicarbonate as a medium.

In addition, since these carbonate- and/or bicarbonate-iron whey proteolysate complexes use a protein hydrolysate complex, the whey proteolysate complexes do exceedingly well in dissolving, digesting, and absorbing, as compared with carbonate and/or bicarbonate-iron lactoferrin substance complex, and carbon- and/or bicarbonate-iron-casein complexes having large molecular weights.

Moreover, it is superior in balancing amino acids since whey protein is used as a raw material. It is also good to use a raw protein material which contains iron and which has a good flavor, i.e., no bitter taste easily produced by the process of hydrolyzing protein with proteolytic enzyme.

An iron-whey proteolysate complex obtained in an embodiment of the present invention can include 1 to 1,000 atoms of iron and at least one molecule of bicarbonate per one molecule of whey protein as measured before proteolysis of whey protein. Further, an iron-whey proteolysate complex in another embodiment has an average molecular weight of 10,000 or less (preferably 3,000 or less).

DETAILED DESCRIPTION OF THE PREFERRED EMBODIMENT

Figure 1:
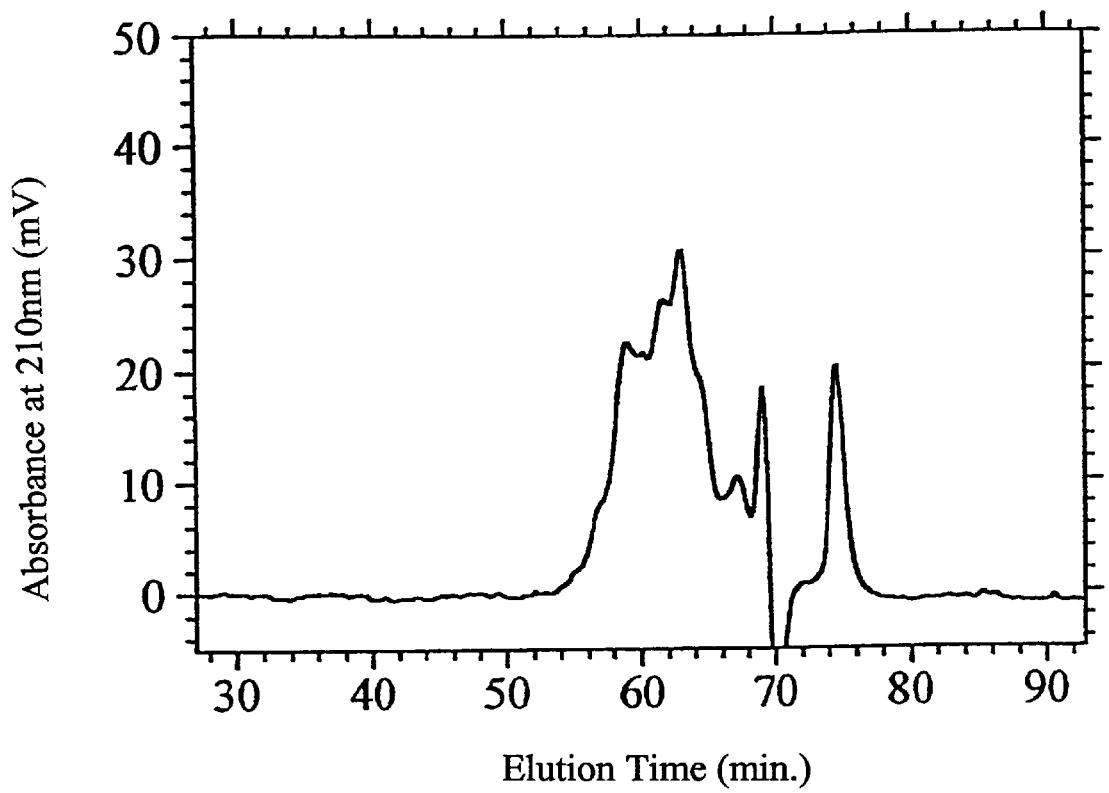
FIG. 1 shows the molecular weight distribution profile of whey proteolysate obtained in Example 1.

The following are the details of the present invention.

Any proteolysis substances treated by a proteolytic enzyme can be used for whey proteolysate of the present invention. A starting material for whey proteolysate to be used in the present invention can be whey protein separated from secretions such as mammal's milk including human or cow milk, or substances separated from whey protein into β-lactoglobulin, and α-lactalbumin. The starting material can also be formed from microorganisms, animal cells, or transgenic animals by using genetic engineering techniques. When using severally mixed protein components as a whey protein, the average molecular weight is calculated by the ratio of each component, and the molality of the dissolved whey protein is calculated from the molecular weight.

The proteolytic enzymes for hydrolysis of whey protein are as follows: trypsin, chymotrypsin, and pepsin from animals; papain, bromelain, and ficin from plants; proteolytic enzymes from microorganisms such as mold, bacteria, and yeast; and proteolytic enzymes produced with genetic engineering techniques. These enzymes can be either refined ones, or unrefined ones, or any enzyme on the market. When the enzyme originates from microorganisms, a culture of microorganisms, a culture solution without microorganisms, and microorganisms themselves can be used, in addition to individually separated enzymes.

For preparing whey proteolysate of the present invention, the normal manufacturing procedure of proteolysis may be followed; in other words, one or more kinds of proteolytic enzyme are added to the whey protein and incubated for a necessary period at a predetermined pH and temperature.

There is no limit in the degree of hydrolysis by the enzyme, but it will be more effective in the present invention if the molecular weight is under 10,000, or under 3000, favorably. It is acceptable to collect only substances of a molecular weight of no more than 3,000, and which are obtained by using an ultrafiltration or chromatography such as gel filtration. If necessary, hydrolytic substances can be refined with normal procedures. These manufactured whey proteolysates can be used in the form of a solution, or powder which can be obtained by freeze-drying or spray-drying used in the conventional manufacturing process of proteolysate.

A carbonate- and/or bicarbonate-iron-whey-proteolysate complex of the present invention is produced by the mixing of (i) a carbonate, (ii) a bicarbonate or (iii) a solution containing a carbonate and a bicarbonate (solution A), and (iv) a solution containing iron (solution B1) and (v) a whey proteolysate solution made by hydrolyzing whey protein with a proteolytic enzyme (solution B2). In various embodiment, (vi) the molality of iron ions of solution B1 may be no more than 1/3, preferably 1/10, or more preferably 1/30, or even more preferably 1/60, and most preferably 1/100, of carbonate or bicarbonate ions dissolved in the solution. (vii) The number of moles of whey proteolysate of solution B2, which is calculated before the whey protein is hydrolyzed, must be in the range of 1 to 1/1000 of the molality of iron ions of solution B1.

Solution A, solution BI and solution B2 can be mixed at the same time, or solution B1 can be added after mixing solution A and solution B2. Alternatively, a mixed solution of solution B1 and solution B2 can be added into solution A or solution A can be added after mixing solution B1 and solution B2. Moreover, it is acceptable to add more carbonate and /or bicarbonate iron than can dissolve, to maintain the molality of carbonate iron and bicarbonate iron constantly at a high level. Yet alternatively, (i) a carbonate, (ii) a bicarbonate or (iii) a carbonate and bicarbonate solution can be added while mixing solution B1 and solution B2 to solution A. In the present invention, a carbonate and/or bicarbonate can be added either in the form of an acid or a water soluble salt. Iron can be added in the form of a water soluble salt. Moreover, in the present invention, (i) a carbonate and/or bicarbonate, (ii) iron and (iii) whey proteolysate can be added in the form of solution, and salt groups can be added in the form of a solid. Also, (i) a carbon and/or bicarbonate, (ii) iron and (iii) whey proteolysate in solid form can be dissolved at the same time. However, procedures, wherein (i) a carbonate and/or bicarbonate and (ii) iron are exclusively dissolved in a solution, must be avoided.

Examples of a carbonate and a bicarbonate are carbonic water, ammonium bicarbonate, sodium bicarbonate, potassium bicarbonate, sodium carbonate, and calcium carbonate. Examples of iron compounds that can be used in the present invention are trivalent iron compounds such as iron (III) chloride, iron (III) nitrate, and iron (III) sulfate, and bivalent iron compound such as iron (II) nitrate, iron (II) sulfate, and iron (II) citrate. Sodium hydroxide, ammonia, potassium hydroxide, hydrochloric acid, citric acid and lactic acid can also be added as an adjuster of pH. The pH is normally adjusted to 2 to 9, and in another embodiment, the pH may be adjusted to 4 to 9. Having the characteristics of having no specific iron taste, adjusted carbon- and/or bicarbonate-iron-whey proteolysate complexes are useful as raw materials in foods, pharmaceuticals, and animal feed.

With reference to examples, and comparative examples, the present invention will be explained as follows:

EXAMPLE 1

Solution C: 1 L of solution containing 1,200 mmole of sodium bicarbonate

Solution D: 0.2 L of solution containing iron (III) chloride having 20 mmole of iron.

Solution E: 0.8 L of solution containing 0.1 mmole of whey proteolysate as calculated before enzymatic hydrolysis.

Average molecular weight was used for adjusting molar concentration. Average molecular weight was calculated from the ratio of each protein constituent and molecular weight, which was computed from the result of sodium dodecyl sulfate (SDS)-polyacrylamide gel electrophoresis.

Whey proteolysate to be used in solution E was produced by the following procedure.

After dissolving one kg of whey protein concentrate with a purity of 80% (originated by New Zealand Daily Board) into 19 kg of deionized water and adjusting pH to 8, 400,000 units of Alcalase 2.4L (Novo Nordisk), and 4,000,000 units of Actinase AS (Kaken Pharmaceutical) were added and hydrolyzed for 5 hours at 50° C. while maintaining pH at 8. The enzyme was inactivated by heating the solution for 10 minutes at 85° C. after adjusting the pH to 7, and the solution was cooled. By filtering using an ultrafiltration membrane of 3,000-fraction molecular weight, whey proteolysate was obtained.

The molecular weight of this hydrolysate was determined with a gel filtration. That is, the hydrolysate was applied to high performance liquid chromatography equipped with a TSKgel G3000PWXL column (300×7.8 mm, Tosoh), and eluted with 55% acetonitrile containing 0.1% trifluoroacetic acid at a flow rate of 0.3 mL/min. The elute was monitored with the absorbence at 210 nm. The same procedure was applied to standard proteins and peptides with known molecular weights, and their elution time was measured. The molecular weights of standard proteins and peptides, and their elution time are shown in Table 1.

TABLE 1

| Standard protein and Peptide | Molecular Weight | Elution Time |
|---|---|---|
| αs-casein | 23,000 | 39.8 (minutes) |
| β-casein | 24,000 | 40.0 |
| aprotinin | 6,500 | 48.8 |
| insulin B-chain | 3,496 | 51.8 |
| insulin A-chain | 2,532 | 55.2 |
| angiotensin | 1,046 | 58.7 |
| glutathione | 307 | 64.2 |

The molecular weight distribution of whey proteolysate was measured based on the relationship between the molecular weights of the standard proteins and peptides and their elution time. The results are shown in FIG. 1. As shown in the figure, the molecular weight of this whey proteolysate was no more than 3,000.

After making one liter of solution (D+E) by mixing 0.2 liter of the above-mentioned solution D and 0.8 liter of solution E, this solution (D+E) was added into one liter of solution C to produce a bicarbonate-iron whey proteolysate complex. Cloudiness or precipitation was not observed in this solution. This solution containing the bicarbonate-iron-whey proteolysate complex was subjected to dialysis and freeze-drying to isolate the bicarbonate-iron-whey proteolysate complex.

The complex obtained above was determined to include 200 atoms of iron and 12,000 molecules of bicarbonate per one molecule of whey protein as measured before whey proteolysis.

EXAMPLE 2

Solution F: 1 L of solution containing 1,200 mmole of sodium bicarbonate.

Solution G: 0.2 L of solution containing iron (III) chloride having 20 mmole of iron.

Solution H: 0.8L of solution containing 0.1 mmole of whey proteolysate as calculated before enzymatic hydrolysis.

Figure 2:
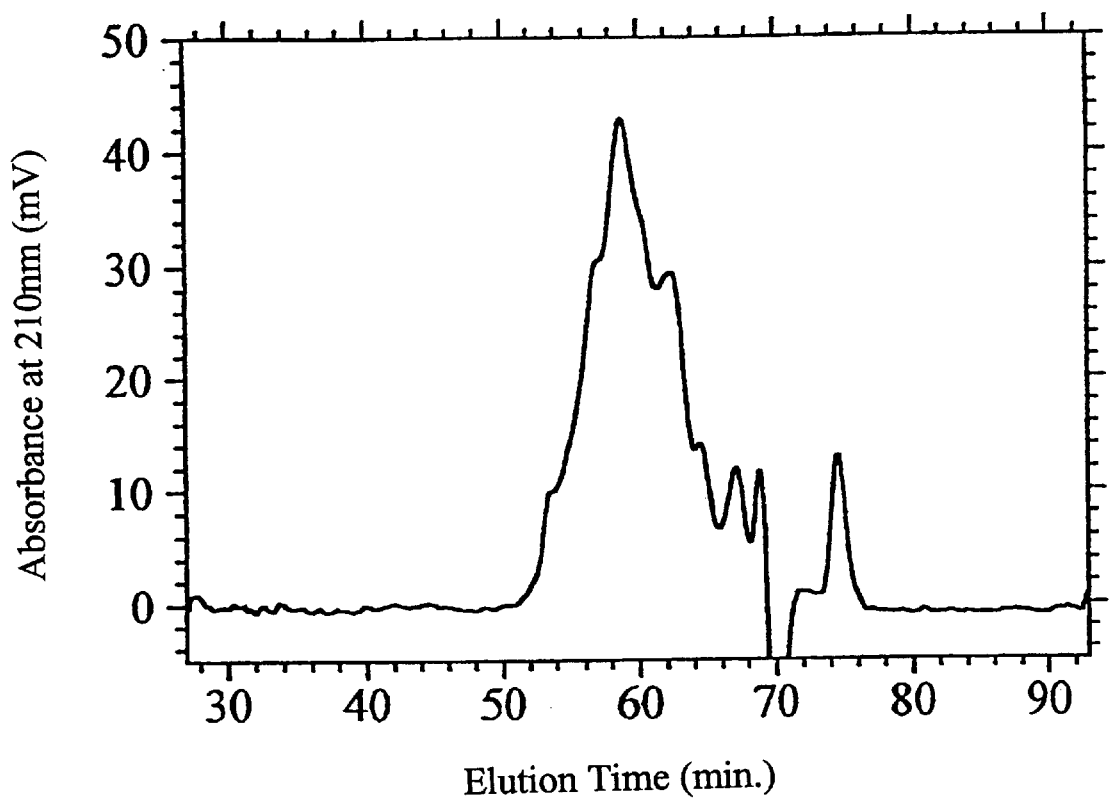
FIG. 2 shows the molecular weight distribution profile of whey proteolysate obtained in Example 2.

The average molecular weight was used for adjusting the molality as in Example 1. The whey proteolysate to be used in solution H was made by the following procedures:

After dissolving one kg of whey protein concentrate with a purity of 80% (originated by New Zealand Daily Board) into 19 kg of deionized water and adjusting pH to 8, 400,000 units of Alcalase 2.4L (Novo Nordisk), and 4,000,000 units of Actinase AS (Kaken Pharmaceutical) were added and hydrolyzed for 5 hours at 50° C. while maintaining pH at 8. After adjusting the pH to 3, 160,000,000 units of Orientase 20A (Hankyu Bio-Industry) were added to the solution and the whey protein was hydrolyzed while maintaining the solution at 50° C. for 16 hours. After adjusting the pH to 7, the enzyme was inactivated by heating the solution for 10 minutes at 85° C., which was then cooled. By filtering using an ultrafiltration membrane of 3,000-fraction molecular weight, whey proteolysate was obtained. By measuring the molecular distribution of this whey proteolysate as in Example 1, it was found that the molecular weight was no more than 1,500. The results are shown in FIG. 2.

After making one liter of solution (G+H) by mixing 0.2 liter of the above-mentioned solution G and 0.8 liter of solution H, this solution (G+H) was added into one liter of solution F to produce a bicarbonate-iron whey proteolysate complex. Cloudiness or precipitation was not observed in this solution. This solution containing the bicarbonate-iron-whey proteolysate complex was subjected to dialysis and freeze-drying to isolate the bicarbonate-iron-whey proteolysate complex.

The complex obtained above was determined to include 200 atoms of iron and 12,000 molecules of bicarbonate per one molecule of whey protein as measured before whey proteolysis.

COMPARATIVE EXAMPLE 1

Solution I: 1 L of solution containing 1,200 mmole of sodium bicarbonate

Solution J: 0.2 L of solution containing iron (III) chloride having 20 mmole of iron.

Solution K: 0.8 L of solution containing 0.1 mmole of whey protein concentrate (New Zealand Daily Board).

The average molecular weights was used for adjusting the molality as in Example 1.

After making one liter of solution (J+K) by mixing 0.2 liter of the above-mentioned solution J and 0.8 liter of solution K, this solution (J+K) was added into one liter of solution I. Cloudiness and precipitation were observed in this solution. This solution containing the bicarbonate-iron-whey protein complex was subjected to dialysis and freeze-drying to isolate the bicarbonate-iron-whey protein complex.

TEST EXAMPLE 1

The following sensual evaluation tests were performed regarding the bicarbonate-iron-whey proteolysate complexes of Examples 1 and 2, and the bicarbonate-iron-whey protein complex of Comparative Example 1. The bicarbonate-iron-whey proteolysate complexes and the bicarbonate-iron-whey protein complex were dissolved at an iron concentration of 3.6 mmole/L in a buffer solution (a simulated buffer solution) simulating a liquid food having a pH of 7.5 which contained 0.05 mole/L of imidazol and 0.15 mole/L of sodium chloride. A panel of 10 men and 10 women was selected to judge whether the solutions had an iron taste wherein the simulated buffer solution was used as a control. The panelists wore blindfolds to eliminate factors related to the appearances. One control and one sample were tested at one time in this order. There was at least one day apart between a test for one sample and a test for another sample. To eliminate day-factor deviation, each panelists evaluated samples in random sequence. The same sensual tests were conducted for a simulated buffer solution dissolving iron (II) sulfate at an iron concentration at 3.6 mmole/L as a sample exhibiting an iron taste. Table 2 shows the number of panelists who sensed an iron flavor in the sensual evaluation tests.

TABLE 2

| Samples | Number of panelists sensed iron flavor |
|---|---|
| Example 1 | 0/20 |
| Example 2 | 0/20 |
| Comparative Example 1 | 20/20 |
| Iron (II) sulfate | 20/20 |

As shown above, it is understood that the two bicarbonate-iron-whey proteolysate complexes of Example 1 and Example 2 exhibit no specific iron taste.

As shown in Example 1 and Example 2, by using whey proteolysate substances, bicarbonate-iron-proteolysate complexes having no specific iron flavor can be produced.

Effects of Embodiments of Invention

A carbonate- and/or bicarbonate-iron-whey proteolysate complex of the present invention has a characteristic of giving no specific iron taste and thus is beneficial as a raw material for drugs, foods, drinks, and animal feed for the purposes of an iron supplement for treatment and prevention of anemia. Since whey protein is used as the raw material, it contains well-balanced amino acids. In addition, it has no bitter taste easily produced through the process of hydrolyzing protein with a proteolytic enzyme. Therefore, the complex is useful as a protein source containing iron with a good flavor.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A carbonate- and/or bicarbonate-iron-whey proteolysate complex, wherein iron and whey proteolysate are coupled via carbonate and/or bicarbonate, said complex having the following characteristics:
    (1) including 1 to 1,000 atoms of iron and at least one molecule of carbonate and/or bicarbonate per one molecule of whey protein as measured before whey proteolysis; and
    (2) exhibiting no metallic taste specific to iron.

2. The complex according to claim 1, wherein the whey proteolysate has an average molecular weight of 10,000 or less.

3. The complex according to claim 2, wherein the whey proteolysate has an average molecular weight of 3,000 or less.

4. A method of producing a carbonate- and/or bicarbonate-iron-whey proteolysate complex, comprising the steps of:

proteolyze whey protein to obtain a whey proteolysate;

mixing (i) a carbonate and/or bicarbonate, (ii) iron, and (iii) the whey proteolysate in a solution having a pH of 2–9, wherein the whey proteolysate is present in the solution when dissolving the carbonate and/or bicarbonate and the iron;

forming a carbonate- and/or bicarbonate-iron-whey proteolysate complex in the solution; and recovering the carbonate- and/or bicarbonate-iron-whey proteolysate complex.

5. The method according to claim 4, wherein the solution includes 1 to 1,000 atoms of iron and at least one molecule of carbonate and/or bicarbonate per one molecule of whey protein as measured before the proteolysis of whey protein.

6. The method according to claim 4, wherein the proteolysis is conducted until the average molecular weight of whey proteolysate is 10,000 or less.

7. The method according to claim 6, wherein the proteolysis is conducted until the average molecular weight of whey proteolysate is 3,000 or less.

8. An iron-enriched food product comprising a carbonate- and/or bicarbonate-iron-whey proteolysate complex according to claim 1, and a food carrier.

9. An iron-enriched animal feed comprising a carbonate- and/or bicarbonate-iron-whey proteolysate complex according to claim 1, and an animal feed carrier.

10. A pharmaceutical for an iron supplement comprising a carbonate- and/or bicarbonate-iron-whey proteolysate complex according to claim 1, and a pharmaceutically acceptable carrier.

* * * * *